United States Patent [19]
Domb

[11] Patent Number: 6,127,448
[45] Date of Patent: Oct. 3, 2000

[54] BIOCOMPATIBLE POLYMERIC COATING MATERIAL

[75] Inventor: Abraham Jacob Domb, Efrat, Israel

[73] Assignee: Alomone Labs Ltd., Jerusalem, Israel

[21] Appl. No.: 09/189,101

[22] Filed: Nov. 9, 1998

[30] Foreign Application Priority Data

Oct. 11, 1997 [IL] Israel ......................................... 122153

[51] Int. Cl.$^7$ .............................. C12P 1/00; C12N 11/04
[52] U.S. Cl. ......................... 523/105; 525/54.1; 530/402; 530/403; 530/405; 435/41; 435/182; 436/528; 436/529; 436/531
[58] Field of Search ........................... 523/105; 525/54.1; 530/402, 403, 405; 435/41, 182; 436/528, 429, 531

[56] References Cited

PUBLICATIONS

Gospodarowicz, D., et al, "Permissive Effect of the Extracellular Matrix on Cell Proliferation In Vitro," *Proc. Natl. Acad. Sci. USA*, 77:4094–4098 (1980).

Tuan, T.L., et al, "In Vitro Fibroplasia: Matrix Contraction, Cell Growth,and Collagen Production of Fibroblasts Cultured in Fibrin Gels," *Exp. Cell. Res.*, 223:127–134(1996).

Underwood, P.A., et al, "The Effect of Extracellular Matrix Molecules on the In Vitro Behaivor of Bovine Endothelial Cells," *Exp. Cell. Res.*, 205:311–319 (1993).

Zhou, L., et al, "Adhesion of Human Trabecular Meshwork Cells to Extracellular Matrix Proteins, Roles and Distribution of Integrin Receptors," *Invest. Ophthalmol. Vis. Sci.*, 37(1):104–113 (1996).

Narumiya, S., et al, "Pre–B Cells Adhere to Fibronectin Via Interactions of Integrin Alpha 5/alpha V with RGDS as well as of integrin alpha 4 with two distinct V Region Sequences at its different binding sites," *Int. Immunol.*, 6:(1)139–147 (1994).

Lydon, M.J., et al, "Cellular Interactions With Synthetic Polymer Surfaces in Culture," *Biomaterials* 6:396–402 (1985).

Strauss, O., et al, "Extracellular Matix Proteins as Substrate Modulate The Pattern of Calcium Channel Expression in Cultured Rat Retinal Pigment Epithelial Cells," *Pflugers Arch–Eur J. Physiol.*, 429:137–139 (1994).

Carnegie, J.A., et al, "Extracellular Matrix Composition and Resilience: Two Parameters that Influence the In Vitro Migration and Morphology of Rat Inner Cell Mass–Derived Cells," *Biol. Reprod.*, 48:287–299 (1993).

Rhodes, D., et al, "Extracellular Matrix Constituents Affect Superficial Gastric Epithelial Cell Adhesion," *J. Gastroenterol. Hepatol.*, 9:S72–S77 (1994).

Paulus, W., et al, "Collagens, Integrins and the Mesenchymal Drift in Glioblastomas: A Comparison of Biopsy Specimens, Spheriod and Early Monolayer Cultures," *Int. J. Cancer*, 58:841–846 (1994).

Kato, S., et al, "Chondroitin Sulfate Immobilized onto Culture Substrates Modulates DNA Synthesis, Tyrosine Aminotransferase Induction, and Intercellular Communication in Primary Rat Hepatocytes," *Cell. Struct. Funct.*, 20:199–209 (1995).

Kita, H., et al, "Extracellular Matrix Proteins Attenuate Activation and Degranulation of Stimulated Eosinophils," *J. Immunol.*, 156:1174–1181 (1996).

Silva, T.M., et al, "Influence of Cell Surface Hydrophobicity on Attachment of Candida Albicans to Extracellular Matrix Proteins," *J. Med. Vet. Mycol.*, 33:117–122 (1996).

Zhang, M., et al, "Epidermal Growth Factor Modulates Cell Attachment to Hyaluronic Acid by the Cell Surface Glycoprotein CD44," *Clin. Exp. Metastasis*, 14:268–276 (1996).

Rollason, G., et al, "Preliminary Report of Cell Culture on a Thermally Reversible Copolymer," *Biomaterials*, 14:153–155 (1993).

Stracke, M., et al, "Cytoskeletal Agents Inhibit Motility and Adherence of Human Tumor Cells," *Kidney Int.*, 43:151–157 (1993).

Viktorov, I.V., et al, "The Use of Polyethylenimine Substrate for Cultivation of Dissociated Cells of the Central Nervous System," *Tsitologiya*, 32(7): 749–752 (1990). (English Abstract).

Watts, K.C., et al, "The Use of Cationic Polyelectrolytes in the Preparation of Cell Monolayers for Automated Cell Scanning and Diagnostic Cytopathology," *Anal. Quant. Cytol.*, 6:272–278 (1984).

*Primary Examiner*—Nathan M. Nutter
*Attorney, Agent, or Firm*—Flehr Hohbach Test Albritton & Herbert LLP; David J. Brezner, Esq.; Renee M. Kosslak, Esq.

[57] ABSTRACT

The invention provides a biocompatible polymeric coating material, wherein the polymeric material is selected from the group consisting of linear, dendrimeric and branched polymers which contain primary, secondary, tertiary or quaternary amine groups with hydrophobic side chains and which polymers are insoluble, or only slightly soluble, in aqueous solution at a pH range between 3 and 11 and soluble in at least one organic solvent selected from the group consisting of alcohols, acetone, methyl ethyl ketone, tetrahydrofuran, dioxane, chloroform, dichloromethane, hexanes and mixtures thereof.

26 Claims, No Drawings

BIOCOMPATIBLE POLYMERIC COATING MATERIAL

The present invention relates to a biocompatible, polymeric coating material. More particularly, the present invention relates to a biocompatible, polymeric coating material which can be used as a coating material for cell growth culture plates and flasks and in combination with other cell culture substrates, as well as in combination with medical devices. The term "biocompatible" as used herein, is intended to denote a material that upon contact with a living element such as a cell or tissue, does not cause toxicity.

Maintaining cells in culture is essential for studying all aspects of clinical and basic research such as cell differentiation and assaying drugs and toxins. The rapid development in cell research and tissue engineering raised the need for maintaining many different types of cells in culture. In order to use cells in culture successfully, they must adhere properly to the substrate. The application of polystyrene plates and flasks for growing cells is widely accepted. However, the polystyrene surface does not provide a satisfactory adhesive surface for most cell types. Thus, a procedure for coating plates is essential. Coating must take into account the properties of cell membranes and their natural substrate. Mammalian cell surfaces generally contain a negatively charged layer of Glycocalyx composed of glycoproteins and proteoglycanes, a group of integral- and associated-membrane proteins. It is therefore expected that a positively charged surface will enable electrostatic interactions with cells. However, existing such substrates are very simplistic, and many cell types will not grow properly on such surfaces (e.g., poly L-lysine coated plates).

Naturally, cells secrete a mixture of proteins which serve as a 'glue' allowing cells to migrate, differentiate or proliferate. Such proteins comprise the extracellular matrix (ECM) which may serve as a substrate in case of a cell layer, or resides in the intercellular space, in cases of a tissue or organ (Gospodarowicz, D., Delgado, D. and Vlodavsky, I. (1980) Permissive effect of the extracellular matrix on cell proliferation in vitro. Proc. Natl. Acad. Sci. U.S.A., 77, 4094–4098., 1980; Tuan, T. L., Song, A., Chang, S., Younai, S. and Nimni, M. E. (1996) In vitro fibroplasia: matrix contraction, cell growth, and collagen production of fibroblasts cultured in fibrin gels. Exp Cell Res, 223, 127–134; (Underwood, P. A. and Bennett, F. A. (1993) The effect of extracellular matrix molecules on the in vitro behavior of bovine endothelial cells. Exp Cell Res, 205, 311–319; and Zhou, L., Zhang, S. R. and Yue, B. Y. (1996) Adhesion of human trabecular meshwork cells to extracellular matrix proteins. Roles and distribution of integrin receptors. Invest Ophthalmol Vis Sci, 37, 104–13). Adhesion of human trabecular meshwork cells to extracellular matrix proteins. Roles and distribution of integrin receptors. Invest Ophthalmol Vis Sci, 37, 104–13). Proteoglycanes on the cell membrane bind to the ECM which is composed of collagen, elastin, fibronectin, laminin, glycosaminoglycans and other unidentified proteins. In addition, unique sets of integrins on cell surface participate in cell-cell interactions, thus, reshaping the cell morphology via cytoskeleton elements (Narumiya, S., Abe, Y., Kita, Y., Miyake, K., Nakajima, K., Watanabe, T. X., Oka, Y., Sugiyama, H., Yagita, H., Okumura, K. and et, al. (1994). Pre-B cells adhere to fibronectin via interactions of integrin alpha 5/alpha V with RGDS as well as of integrin alpha 4 with two distinct V region sequences at its different binding sites. Int Immunol, 6, 139–47; Zhou, et al. ibid). The molecular identification of components from the ECM, postulated a central role in cell adhesion to filamentous proteins such as fibronectin and collagen (Lydon, M. J., Minett, T. W. and Tigha, B. J. (1985) Cellular interactions with synthetic polymer surfaces in culture. Biomaterials, 396–402). However, these components are biologically active as was demonstrated in many systems. For example, the expression of calcium channels was altered by changing the ECM composition in cultured rat retinal epithelial cells (Strauss, O. and Wienrich, M. (1994) Extracellular matrix proteins as substrate modulate the pattern of calcium channel expression in cultured rat retinal pigment epithelial cells. Pflugers Arch, 429, 137–139). Several systematic studies demonstrated that various components of the ECM such as laminin, fibronectin, collagen I and IV, vitronectin (Strauss, O. and Wienrich, M. (1994) Extracellular matrix proteins as substrate modulate the pattern of calcium channel expression in cultured rat retinal pigment epithelial cells. Pflugers Arch, 429, 137–139) or Matrigel (a tumor cell-derived basement membrane preparation; (Carnegie, J. A. and Cabaca, O. (1993) Extracellular matrix composition and resilience: two parameters that influence the in vitro migration and morphology of rat inner cell mass-derived cells. Biol Reprod, 48, 287–99), affect different properties such as cell proliferation, adhesion and spreading. Alteration of biological properties by the composition of the substrate was reported for variety of cells and tissues e.g., superficial gastric epithelial cell (Rhodes, D., Revis, D. and Lacy, E. R. (1994). Extracellular matrix constituents affect superficial gastric epithelial cell adhesion. J Gastroenterol Hepatol), and bovine endothelial cells; (Underwood, et al. ibid) The various effects on cell biology properties by ECM composition reflect the activation of ECM receptors—the integrins, and their signaling pathways (Paulus, W., Huettner, C. and Tonn, J. C. (1994). Collagens, integrins and the mesenchymal drift in glioblastomas: a comparison of biopsy specimens, spheroid and early monolayer cultures. Int J Cancer, 58, 841–846). Thus, the ability of the ECM to alter cellular properties such as growth, migration, morphology and differentiation (Kato, S., Sugiura, N., Kimata, K., Kujiraoka, T., Toyoda, J. and Akamatsu, N. (1995) Chondroitin sulfate immobilized onto culture substrates modulates DNA synthesis, tyrosine aminotransferase induction, and intercellular communication in primary rat hepatocytes. Cell Struct. Funct., 20, 199–209; Kita, H., Horie, S. and Gleich, G. J. (1996) Extracellular matrix proteins attenuate activation and degranulation of stimulated eosinophils. J Immunol, 156, 1174–81; Silva, T. M., Glee, P. M. and Hazen, K. C. (1995) Influence of cell surface hydrophobicity on attachment of Candida albicans to extracellular matrix proteins. J Med Vet Mycol, 33,117–122; Underwood, et al. ibid; Zhang, M., Singh, R. K., Wang, M. H., Wells, A. and Siegal, G. P. (1996) Epidermal growth factor modulates cell attachment to hyaluronic acid by the cell surface glycoprotein CD44. Clin Exp Metastasis, 14, 268–76), prevent it or its purified from being of general use.

Still, ECM or its purified compounds are being used for specific cells and conditions, including fibrin, collagen, gelatin derivatives and fibronectin. In addition, simple reagents which provides free amino group, such as poly L-lysine, poly D-lysine and polyornitine, are broadly used. For the reasons outlined above, such substrates are of limited use, and some are also difficult to purify, rendering them too expensive for large scale projects.

Thus, a need emerges for improved adhesive substrates for coating plates (Lydon et al., 1985). Primaries cultures, (e.g., from transgenic animals which are studied at the cellular level), the development of in vivo dyes for studying intracellular cell dynamics, microinjection methodologies and more, all require cells to be maintained for many days in culture. A more specific need for a 'good' coating substrate is for maintaining neuronal cell lines. Neuronal cells, need not only to adhere to the surface, but also to extend their processes and to allow appropriate development of growth cones and cell-cell contacts. To this end, synthetic polymers which may replace ECM were developed and their properties as substrates for cell adhesions were evaluated (Rollason, G., Davies, J. E. and Sefton, M. V. (1993) Preliminary report on cell culture on a thermally reversible copolymer. Biomaterials, 14,153–155). The following factors have been investigated: surface hydrophobicity, surface energy of the substrate and surface functional groups. It was found that hydrophobic and/or crystalline surfaces induces cell adhesion. Surfaces containing functional groups such as carboxylic acids, amines and hydroxyl groups improve cell adhesion (Lydon et al., ibid; Paulus et al. ibid; Rollason et al, ibid; Stracke, M. L., Soroush, M., Liotta, L. A. and Schiffmann, E. (1993) Cytoskeletal agents inhibit motility and adherence of human tumor cells. Kidney Int, 43, 151–157; Viktorov, I. V.; Andreeva, N. A.; lsaev, N. K., The use of polyethylenimine substrate for cultivation of dissociated cells of the central nervous system, Tsitologiya (1990), 32(7), 749–52; Watts, K. C., Husain, O. A. and Tucker, J. H. (1984) The use of cationic polyelectrolytes in the preparation of cell monolayers for automated cell scsnning and diagnostic cytopathology. Anal. Quant. Cytol, 6, 272–278).

Cell culture research relies on the use of various plate coating substrate essential for cell attachment and proliferation. The most common substrates are poly-lysine and various cell extracts, mostly purified components of the ECM. These substrates are either inconsistent and irreproducible, or require coating for 24–48 hours prior to plating the cells or both. Furthermore, the coated plate is useful only 1–2 days after coating and the substrates are relatively expensive.

It is therefore the purpose of this invention to develop a novel series of biologically compatible, reproducible, effective and inexpensive cationic substrates for coating cell culture plates with storage stability of months. For the adhesive compound to satisfy the needs of cell cultures the following criteria were set:

1. Surface activity that allows normal cell function and proliferation.
2. A hydrophilic cationic polymer that is insoluble or slightly soluble in water.
3. Transparent so the cells can be viewed through the plate.
4. Not toxic and preferably biologically inert.
5. Uniform distribution on the plate after application;
6. Can be prepared in a commercial scale and quality at an affordable cost.
7. Active for months after coating of the plate.

With the above criteria in mind, there is now provided according to the present invention a biocompatible polymeric coating material, wherein said polymeric material is selected from the group consisting of linear, dendrimeric and branched polymers which contain primary, secondary, tertiary or quaternary amine groups with hydrophobic side chains and which polymers are insoluble, or only slightly soluble, in aqueous solution at a pH range between 3 and 11 and soluble in at least one organic solvent selected from the group consisting of alcohols, acetone, methyl ethyl ketone, tetrahydrofuran, dioxane, chloroform, dichloromethane, hexanes and mixtures thereof.

In preferred embodiments of the present invention there is provided a biocompatible polymeric coating material comprising a hydrophobic cationic polymer which is at most slightly soluble in aqueous solution and which is soluble in organic solvents, said polymer being selected from the group consisting of at least partially alkylated polyethyleneimine (PEI); at least partially alkylated poly(lysine); at least partially alkylated polyornithine; at least partially alkylated poly (amido amine), at least partially alkylated homo- and co-polymers of vinylamine; at least partially alkylated acrylate containing aminogroups, copolymers of vinylamine containing aminogroups with hydrophobic monomers, copolymers of acrylate containing aminogroups with hydrophobic monomers, and amino containing natural and modified polysaccharides and mixtures thereof.

Especially preferred polymers are polyethylene imine (PEI), amidoamine and amine dendrimers and polylysine.

The term "insoluble", as used herein, is intended to denote polymer solubility of less than 0.1 mg/ml, while the term "slightly soluble" is intended to denote polymer solubility of about between 1 and 5 mg/ml. "Soluble" is used to denote polymer solubility above 10 mg/ml.

Preferred hydrophobic side chains include liner or branched fatty chains of $C_6$ to $C_{22}$, non-degradable short polymer chains of molecular weights between 300 and 2000 of the structures, poly(alkyl acrylate), poly(alkyl methacrylate), poly(caprolactone), poly(lactide), and poly (glycolide).

The polymers that are the object of this invention are polyamines that are soluble in alcohol and slightly soluble in aqueous solution and which can be applied on the culture plates from an alcohol containing solution. The polymers of the present invention are hydrophilic insoluble or slightly soluble in aqueous solution but soluble in at least one organic solvent, preferably, alcohol or alcohol/water solutions.

As is known, dendrimeric polymers are highly branched, well structured, three dimensional polymers, which are usually spherical and which are prepared by step polymerization, wherein at each step one more layer of polymer units is added.

The cationic nature of the polymer and its solubility properties provide the desired coating. The alkyl side groups encores the PEI to the hydrophobic surface of the plastic plate while allowing the PEI chains between encores to hydrate and interact with the cells. The cationic polymer may contain other functional groups that add another function to the coating such as a specific ligand that allows binding of certain cells or antibodies to the surface. The polymers of this invention are useful for altering the surface properties of biodegradable porous beads or sponges for cell growing in tissue engineering procedures. Coating of medical devices such as stents, catheters, vascular grafts, and metal and plastic orthopedic devices with cationic polymers to improve their compatibility with body tissue and body fluid components and avoid complications such as calcification.

The term "encores" as used herein is intended to denote that the modified polyamine sticks to the hydrophobic surface through the hydrophobic chains like encores, which allows the polymer to be retained on the surface, while allowing mobility and swelling of the polycation chains between two hydrophobic encores.

The structures of the polymers on this invention are linear or branched polymers that contain primary, secondary, tertiary or quaternary amine groups with hydrophobic side chains that are insoluble in water at a pH range between 3 and 11 but soluble in common organic solvents or aqueous solutions at pH below 3. The polymers of this invention preferably contain between 3 and 32% w/w of nitrogen as cationic residues. The polymers of this invention include alkylated polyethyleneimines, polyvinylamine, polylysines, polyurnitines, poly(aminoethyl methacrylates) and copolymers, and poly(acryl-lysine). Examples of solutions for the polymers are: ethanol, methanol, propanol, isopropanol, butanol, acetone, methyl ethyl ketone, tetrahydrofuran, dioxane, chloroform, dichloromethane, hexanes and mixtures thereof. The water miscible solvents may contain up to 70% v/v of water.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLES

Example 1
Synthesis of Lipophilic Polyethylene Imine

1. Alkylation with alkyl halides

PEI of 30,000 molecular weight was partially alkylated with linear alkyl halide (chloride or bromide) with a chain length of 10 to 18 methylene groups. The degree of alkylation ranged from 1 to 10% of the amine groups of the PEI. The reaction between dry PEI and the alkyl halide was carried out in a dry organic solvent (toluene, chloroform or dimethylformamide) at reflux for a few hours. The alkylation yield was determined by NMR analysis. The solubility of the polymer in alcohol and in water was determined.

Alkylated PEI containing 2 to 5% stearyl groups were insoluble in water but were soluble in alcohol. These PEI derivatives of molecular weights between 5,000 and 2,000,000 were used for tissue culture plate coating.

2. Amidation with alkyl halides

PEI was partially alkylated with fatty acid halides (chloride or bromide) or anhydrides with a chain length of 10 to 18 methylene groups. The degree of amidation ranged from 1 to 10% of the amine groups of the PEI. The reaction between dry PEI and the alkyl halide was carried out in a dry organic solvent (toluene, acetone, dichloromethane, chloroform or dimethylformamide) at room temperature for a few hours. The alkylation yield was determined by NMR analysis. In a typical experiment, PEI (1.0 g, Mw=600,000) was dissolved in dichloromethane (10 ml). To the stirred solution was added palmitoyl chloride (50 mg) and the solution was allowed to react overnight. The solvent was evaporated and the polymer was dissolved in cold alcohol. The polymer was soluble in alcohol but not in water.

Alkylated PEI containing 1 to 10% palmitoyl groups were insoluble in water but soluble in alcohol were selected for plate coating.

Example 2
Alkylation of Poly(lysine)

Polylysine was hydrophobized to become insoluble in water by the attachment of alkyl groups of 5 to 20 methylene groups by reacting alkyl halide with the polymer in dichloromethane or by amidation of the free amino side groups with alkanoic acid using dicyclohexyl carbodiimide (DCC) in dichloromethane.

Example 3
Alkylation of Poly(vinyl amine) (PVA)

PVA (Mw=7,000) was reacted with decanoyl bromide or anhydride in chloroform solution at a ratio of 2 to 10% per amino groups in the polymer. The reaction was allowed to stir at room temperature for 24 hours where the solvent was evaporated to dryness and the resulted polymer was dissolved in ethanol and precipitated in cold water. The degree of alkylation was determined by NMR spectroscopy from the ratio of the aliphatic methylene peaks and the methylene peaks adjacent to the amino groups.

Example 4
Preparation of Acrylate Based Cationic Polymers

To a polymerization kettle equipped with a stirrer and a nitrogen inlet was added N,N-dimethylamino ethyl methacrylate (30 g), amino ethyl methacrylate (30 g), lauryl methacrylate (60 g), benzoyl peroxide (1.0 g) and dry toluene (300 ml). The kettle was immersed into a water bath at 70° C. and allowed to stir overnight. After cooling to room temperature, diethyl ether (500 ml) as added and the white polymer precipitate was isolated by filtration and washed twice with diethylether and dried at room air. The polymer was soluble in organic solvents but insoluble in water. Other monomers such as alkylacrylate were used to coat tissue culture plates and the properties were determined using the method described in Example 8.

Polymers of different ratio of these monomers have been prepared using a similar procedure. Other monomers such as alkylcrylate or methacrylate with alkyl chains of 5 to 20 methylene, dimethyl amino and aminoalkyl methacrylates or acrylate were prepared. Thus, polycationic coatings that contain functional groups such as phosphatidyl choline or a ligands for selective attachment of biological substances selected from the group consisting of cells, antibodies, hormones or receptors, or markers and dyes such as flurorescent dye and analytical markers are prepared according to the invention.

Example 5
Preparation of Hydrophobic Acrylate Polymer for Stent Coating:

Biotin methacrylate was prepared from the reaction of methacryloyl chloride and biotin hydrazine in chloroform solution with triethylamine as acid acceptor. The reaction mixture was added to water and biotin methacrylate was isolated by filtration. This monomer was copolymerized with N,N-dimethylamino ethyl methacrylate and lauryl methacrylate to form a water insoluble polymer. The polymer is useful for coating metal stents and surfaces that have a specific affinity to ligands that are attached to the surface using desired avidin-ligand components that are attached via the biotin-avidin complex.

Example 6
Stability of Polymer Solutions

Because of the low concentration of polymer to be used for plate coating, the polymer concentration may decrease with time as a result of absorption to the container. A study was conducted to determine the proper storage container (kind of material and sililatation) and conditions to minimize changes in polymer concentration. It was found that at a concentration of 1 mg/ml, insignificant changes in polymer concentration was observed after storage at room temperature for 6 months. The use of sililated glass bottles or the addition of a few percent of glycerin, polyethylene glycol or arabinogalactan improved polymer concentration during storage.

Example 7
Coating of Plates

Standard polystyrene culture plates were coated with alkylated PEI by pouring or spraying increasing amounts of an alcoholic solution of the polymer (1.0 ml of a 0.01 mg/ml polymer (1.5 mole % stearate derivatized PEI) in alcohol per 10 cm diameter standard plate). The alcoholic solution may contain 2–20% v/v of water/glycerin and other non-interfering additives that protect the coating activity over time. The coated plates were evaluated for content uniformity by the Fluorescamine analysis of the polymer amino groups. The content of the polymer after a series of washings was determined by the fluorescamine method. In all experiments, a uniform coating was obtained. The fluorescamine marker can be bound to the polymer prior to application on the substrate. Other relevant markers are: Rhodamin B, Nynhidrin, and common markers that can be attached to amines.

Example 8
Cell Culture Using P12 Cells

The cell adhesion properties were determined using PC12 neuronal cells. These are carcinogenic cells from the medulla of the adrenal cortex releasing catechol amines. The following protocol was used: to a 24 well tray a polymer solution in alcohol (0.1 ml of 100 mcg/ml) was added. After 30 minutes the solution was removed and dried at room air before sterilization by UV irradiation for 30 minutes. Each well was loaded with a 1 ml containing 200,000 cells. After 72 hours of incubation, the cell concentration and viability were determined by microscopic visualization. The response of the cells to Nerve Growth Factor (NGF) and to Dopamine was also determined as an indication for normal growing cell culture and the inertness of the polymeric coating.

NGF Protocol

Low concentration of cells (100,000 per well) were allowed to adhere to the bottom of the coated well (3–5 hours). NGF was added at a 50ng/ml/day for 3 days and the growing of neurites was measured. Dopamine protocol: High concentration of cells (1,000,000 per well) were allowed to grow for 3 days. The wells were washed with media containing ascorbic acid and radiolabeled dopamine was added and the cells were incubated for two hours at 37° C. The wells were rinsed twice with media to remove non incorporated dopamine and 50 nM KCl solution was added. After 15 min of incubation, samples from the media and from the cells were taken for radioactive counting.

For all experiments, standard polylysine/collagen coating was used as reference.

Results

For both polymer coatings, the cells adhered very well to the surface and proliferate normally without cell death or aggregation. The response to NGF was similar to the reference, after one, two and three days the cells formed neurites at 1,2 and 3 times the size of the cell, respectively. The dopamine release from the cells was similar for all evaluated polymers (40%). FIG. 1 show photographs of a typical PC12 cells growing on polylysine/collagen coating (1A-before NGF, 1B-after NGF) and cationic polymer coating after NGF treatment (1C and 1D). These data indicate that a synthetic cationic polymer does not interfere cell growth and allows normal cell growing, similar to the standard polylysine/collagen coating.

Table 1 summarized the coating properties of various polyamine derivatives tested using the PC12 cell-line.

TABLE 1

Polycation coatings for PC12 cell-line cultures

| Polymer (kDa) | Unit structure | Cell growth | Toxicity | Adhesion | Differentiation with NGF |
|---|---|---|---|---|---|
| Polyethyleneimine- | | | | | |
| 2% N-stearyl | $[N-CH_2-CH_2]_{14}$-$[NH-CH_2-CH_2]_{686}$ $(CH_2)_{17}CH_3$ HCl | 3.00 | – | +++ | +++ |
| 2% N-stearoyl | $[N-CH_2-CH_2]_{14}$-$[NH-CH_2-CH_2]_{686}$ $C(O)$-$(CH_2)_{16}CH_3$ HCl | 3.00 | – | +++ | +++ |
| 2% N-decanyl | $[N-CH_2-CH_2]_{14}$-$[NH-CH_2-CH_2]_{686}$ $(CH_2)_9CH_3$ HCl | 3.00 | – | +++ | +++ |
| 5% N-stearyl | $[N-CH_2-CH_2]_{36}$-$[NH-CH_2-CH_2]_{632}$ $(CH_2)_{17}-CH_3$ HCl | 3.00 | – | +++ | +++ |
| 10% N-methyl | $[N-CH_2-CH_2]_{68}$-$[NH-CH_2-CH_2]_{632}$ $CH_3$ HI | 3.00 | – | +++ | +++ |
| 10% N-pentyl | $[N-CH_2-CH_2]_{680}$-$[NH-CH_2-CH_2]_{632}$ $(CH_2)_4CH_3$ HCl | 3.00 | – | +++ | +++ |
| Polyvinylamine | | | | | |
| 10% N-pentyl | $[-HC(NH)-CH_2]_{53}$-$[HC(NH_2)-CH_2]_{477}$ $(CH_2)_4CH_3$ HCl | 3.00 | – | +++ | +++ |
| 2% N-stearyl | $[-HC(NH)-CH_2]_{53}$-$[HC(NH_2)-CH_2]_{477}$ $(CH_2)_4CH_3$ HCl | 3.00 | – | +++ | +++ |
| poly(N,N-dimethylaminoethyl methacrylate-coc-methylmethacrylate | | 3.00 | – | +++ | +++ |
| | $[CH_2-C(CH_3)]\ldots[CH_2-C(CH_3)]$ $COO-CH_2-CH_2-N(CH_3)_2$ $COO-CH_3$ | 3.00 | – | +++ | +++ |

** PC12 cell growth properties on polystyrene plates coated with the polymer (100 mcg/ml alcohol) was rated in scale of 0 to 3 based on evaluations of the toxicity, cell adhesion and differentiation (72 h after NGF treatrnent).

Example 9
Compatibility of the Polymer for Adhesion Using P19 Cells

Adhesion of cells to a solid phase or to other cells requires a cross-talk between the cells and the substrate. In order to test the applicability of the polymer for cell cultures we are testing the effect of the polymer on growth and neuronal properties of P19 developing neurons. The growth of these neuronal cells is adherence dependent and, moreover, P19 neurons are very sensitive to the substrate as reflected by their ability to extend neurites. Neurite extension is in a good correlation with the physiological state of the neurons. P19 cell-line, a mouse derived embryonic carcinoma, as a model system for neuronal differentiation (McBurney, M. W. (1993) P19 embryonal carcinoma cells. Int. J. Dev. Biol., 37, 135–140). Following aggregation and treatment with retinoic acid these cells differentiate into neurons, astrocytes and fibroblast-like cells (Jones-Villeneuve, E. M., Rudnicki, M. A., Harris, J. F. and McBurney, M. W. (1983) Retinoic acid-induced neural differentiation of embryonal carcinoma cells. Mol. Cell. Biol., 3, 2271–2279; McBurney, ibid). Furthermore, P19 neurons develop typical synapses and are capable of neurotransmitter release (Finley, M. F. A., Kulkarni, N. and Huettner, J. E. (1996) Synapse formation and establishment of neuronal polarity by P19 embryonic carcinoma cells and embryonic stem cells. J. Neurosci., 16,1056–1065; Parnas, D. and Linial, M. (1995) Cholinergic properties of neurons differentiated from an embryonal carcinoma cell-line (P19). Int. J. Dev. Neurosci., 13, 767–781). Thus, the P19 mouse embryonal carcinoma cell line is suitable to analyze regulation of neuronal differentiation. During neuronal differentiation neurons are susceptible to the influence of supporting cells, neurotrophic factors (NTFs) and altered levels of neuronal activity. Thus, the phenotype of P19 neurons is flexible and subject to influences from the surrounding environment. In order to evaluate the applicability of the PEI polymer for growth of the P19 neurons (and eventually of other neuronal cell cultures) non-neuronal cells in the culture were eliminated, thus isolating the adhesive properties of P19 neurons from possible effects of supporting cells.

Cells are cultured and differentiated essentially as described in Rudnicki and McBurney with some modifications. Briefly, cells are aggregated in the presence of 0.5 mM retinoic acid for 4 days. At day 4, the aggregates were treated with trypsin and plated on culture-grade plates coated with poly-L-lysine (10 mg/ml) or with the polymer at various concentrations and solution modifications (ranging from 1–100 mg/ml). The cells are then plated in defined medium—DMEM supplemented with BioGro2 (containing transferrin, insulin, eselenium and ethanolamine) supplemented with fibronectin. Cytosine-b-D-arabinofuranoside is added 1 day after plating, for 2 days in order to eliminate the dividing non-neuronal cells. Medium (without fibronectin) is replaced every 72 h. All media are supplemented with glutamine and with antibiotics. Cells were differentiated and plated on PEI (1.5% stearate modification, Mw=600,000) or standard poly-L-lysine coated plates, and time lapse images are taken, in order to evaluate neurite outgrowth rate. Average neurite length as a function of time is compared between the different substrates and coating protocols. It was already shown that the parameter of neurite growth rate is very sensitive to cell adhesion and to the degree of neuronal maturation (Parnas, D. and Linial, M. (1996) Acceleration of neuronal maturation of P19 g cells by increasing culture density. (submitted)).

Results

In this study we compared solely the survival and adhesion properties which are summarized in the following table.

| P19 cells(12 days) | Adhesion | survival[a] | Comments |
|---|---|---|---|
| No coating | − | − | No adherence |
| poly L lysine | +++ | +++ | Coating is stable for 2 days |
| Gelatin | + | − | Long lasting coating |
| Polymer - 10 mg/ml | +++++ | + | Stability - greater then 4 days |
| Polymer - 2 mg/ml | ++++ | +++ | Stability - greater then 4 days |
| Polymer - 1 mg/ml | ++ | + | Stability - greater then 4 days |

[a]Survival is determined by counting the cells and measuring protein content in the plate. P19 cells fail to survive on high concentration of the polymer as a result of inhibition of neurite growth rather then inability to adhere to the plates. Long term adhesion is measured by the protein content at the beginning of the experiment relative to the number of cells (as determined by the protein amount) in the end of the culturing period. The physical strength of attachment of the cells to the surface is determined by the number of cells which were resistant to extensive washes by physiological balanced buffer. Other cell-lines have also been used for testing the insoluble polyamines of this invention. The properties of a few cell-lines are summarized in the following table. In an another experiment, agarose beads were coated with modified PEI (2% stearyl alkylation) were cultured with mouse muscle cells. The cells proliferated within the agarose beads much more than in the uncoated beads.

| Cell types | Origin | Presently used substrate | Biological properties |
|---|---|---|---|
| parotid acinar (Moller et al., 1996*) primary dispersed parotid cells, | rat | poly L-lysine | a-amylase release Spreading, Adhesion Survival receptors activation |
| HCG-AZA3 HSY (Myoken et al., 1996**) | human | poly L-lysine | amylase release Spreading, Adhesion Survival |
| C2 (Balogh et al., 1996***) | mouse, myobiast | gelatin | Cell fusion Adhesion Muscle twitching |

*Moller, K., Benz, D., Perrin, D. and Soling, H. D. (1996) The role of protein kinase C in carbachol-induced and of cAMP-dependent protein kinase in isoproterenol-induced secretion in primary cultured guinea pig parotid acinar cells. Biochem. J., 314, 181–187.
**Myoken, Y., Myoken, Y., Okamoto, T., Kan, M., Mckeehan, W. L., Sato, J. D. and Takada, K. (1996) Expression of fibroblast growth factor-1 (FGF-1), FGF-2 and FGF receptor-1 in a human salivary-gland adenocarcinoma cell line: Evidence of autocrine growth. Int J Cancer, 65, 650–657.
***Balogh, A., Mege, R. M. and Sobel, A. (1996) Growth and cell density-dependent expression of stathmin in C2 myoblasts in culture. Exp Cell Res, 224, 8–15.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A biocompatible polymeric coating material, wherein said polymeric material is selected from the group consisting of linear, dendrimeric and branched polymers which contain primary, secondary, tertiary or quaternary amine groups with hydrophobic side chains and which polymers are insoluble, or only slightly soluble, in aqueous solution at a pH range between 3 and 11 and soluble in at least one organic solvent selected from the group consisting of alcohols, acetone, methyl ethyl ketone, tetrahydrofuran, dioxane, chloroform, dichloromethane, hexanes and mixtures thereof.

2. A biocompatible polymeric coating material according to claim 1, comprising a hydrophobic cationic polymer which is at most slightly soluble in aqueous solution and which is soluble in organic solvents, said polymer being selected from the group consisting of at least partially alkylated polyethyleneimine (PEI); at least partially alkylated poly(lysine); at least partially alkylated polyornithine; at least partially alkylated poly(amido amine), at least partially alkylated homo- and co-polymers of vinylamine; at least partially alkylated acrylate containing aminogroups, copolymers of vinylamine containing aminogroups with hydrophobic monomers, copolymers of acrylate containing aminogroups with hydrophobic monomers, and amino containing natural and modified polysaccharides and mixtures thereof.

3. A biocompatible polymeric coating material according to claim 1, wherein said polymer contains between 3 and 32% w/w of nitrogen as cationic residues.

4. A coating substrate for maintaining neuronal cell lines comprising a biocompatible polymeric coating material according to claim 1.

5. A coating for a cell growth culture plate comprising a biocompatible polymeric coating material according to claim 1.

6. A coating for a cell growth culture flask comprising a biocompatible polymeric coating material according to claim 1.

7. A biocompatible polymeric coating material according to claim 1, in combination with a medical device selected from the group consisting of stents, catheters, vascular grafts, and metal and plastic orthopedic devices.

8. A biocompatible polymeric coating material according to claim 1, in combination with a cell culture substrate.

9. A biocompatible polymeric coating material according to claim 1, in combination with a biodegradable porous bead for cell growth.

10. A biocompatible polymeric coating material according to claim 1, in combination with a biodegradable sponge for cell growth.

11. A biocompatible polymeric coating material according to claim 1, wherein said coating is polycationic containing ligands for the selective attachment of biological substances.

12. A biocompatible polymeric coating material according to claim 11, wherein said biological substances are selected from the group consisting of antibodies, hormones and receptors.

13. A biocompatible polymeric coating material according to claim 1, wherein said coating is polycationic and contains a fluorescent dye.

14. A biocompatible polymeric coating material according to claim 1, further comprising glycerine for improved stability.

15. A biocompatible coating material of a polymeric material selected from the group consisting of linear, dendrimeric and branched polymers which contain primary, secondary, tertiary or quaternary amine groups with hydrophobic side chains and which polymers are insoluble, or only slightly soluble, in aqueous solution at a pH range between 3 and 11 and soluble in at least one organic solvent selected from the group consisting of alcohols, acetone, methyl ethyl ketone, tetrahydrofuran, dioxane, chloroform, dichloromethane, hexanes and mixtures thereof.

16. A coating material according to claim 15, wherein the polymeric material is a hydrophobic cationic polymer selected from the group consisting of at least partially alkylated polyethyleneimine (PEI); at least partially alkylated poly(lysine); at least partially alkylated polyornithine; at least partially alkylated poly(amido amine), at least partially alkylated homo- and co-polymers of vinylamine; at least partially alkylated acrylate containing aminogroups, copolymers of vinylamine containing aminogroups with hydrophobic monomers, copolymers of acrylate containing aminogroups with hydrophobic monomers, and amino containing natural and modified polysaccharides and mixtures thereof.

17. A biocompatible coating composition, including a polymeric material as defined in claim 1, together with a ligand for the selective attachment of a biological substance.

18. A biocompatible coating composition according to claim 17, wherein the biological substance is selected from the group consisting of antibodies, hormones and receptors.

19. A biocompatible coating composition, including a polymeric material as defined in claim 1, together with a fluorescent dye.

20. A biocompatible coating composition, including a polymeric material as defined in claim 1, together with an analytical marker.

21. A coating composition according to any one of claims 17, additionally including a carrier solvent selected from the group consisting of alcohols, acetone, methyl ethyl ketone, tetrahydrofuran, dioxane, chloroform, dichloromethane, hexane, mixtures thereof and mixtures of any of the above with water.

22. A coating composition according to any one of claims 17, additionally including an additive selected from the group consisting of glycerin and polyethylene glycol.

23. A coated product including a substrate to which a biocompatible coating composition has been applied, the coating composition including a polymeric material as defined in claim 1.

24. A coated product according to claim 23, wherein the substrate is selected from the group consisting of cell growth culture substrates such as plates, flasks and other vessels; and medical devices such as stents, catheters, vascular grafts and metal and plastic orthopaedic devices.

25. A coated product according to claim 24, wherein the substrate is selected from the group consisting of biodegradable sponges and porous beads for cell growth.

26. A coating composition according to claim 17, in a sililated glass storage vessel.

* * * * *